(12) United States Patent
Cassier et al.

(10) Patent No.: US 8,658,186 B2
(45) Date of Patent: Feb. 25, 2014

(54) FRAGRANCING TRANSPARENT SOLID COMPOSITION BASED ON FATTY ACID SALTS AND ON AN OXYETHYLENATED FATTY ALCOHOL; AND STABILIZATION METHOD

(75) Inventors: Matthieu Cassier, Paris (FR); Fanny Lefebvre, Joinville le Pont (FR)

(73) Assignee: L'Oreal, Paris (FR)

( * ) Notice: Subject to any disclaimer, the term of this patent is extended or adjusted under 35 U.S.C. 154(b) by 379 days.

(21) Appl. No.: 12/706,632

(22) Filed: Feb. 16, 2010

(65) Prior Publication Data

US 2010/0272665 A1    Oct. 28, 2010

Related U.S. Application Data

(60) Provisional application No. 61/154,800, filed on Feb. 24, 2009.

(30) Foreign Application Priority Data

Feb. 17, 2009  (FR) ..................................... 09 51007

(51) Int. Cl.
*A61K 8/02*    (2006.01)

(52) U.S. Cl.
USPC ............................................ 424/401; 424/65

(58) Field of Classification Search
None
See application file for complete search history.

(56) References Cited

U.S. PATENT DOCUMENTS

| 5,407,668 A | 4/1995 | Kellner |
| 5,424,070 A | 6/1995 | Kasat et al. |
| 5,858,336 A * | 1/1999 | Graf et al. ........................ 424/65 |
| 5,863,524 A | 1/1999 | Mason et al. |
| 2003/0206931 A1 | 11/2003 | Moghe et al. |
| 2006/0182773 A1 * | 8/2006 | Bruning et al. ................ 424/401 |

* cited by examiner

*Primary Examiner* — Lezah Roberts
*Assistant Examiner* — Nannette Holloman
(74) *Attorney, Agent, or Firm* — Novak Druce Connolly Bove + Quigg LLP

(57) ABSTRACT

The invention relates to a fragrancing aqueous transparent solid composition in a cosmetically acceptable support:
  a) at least one aqueous phase and
  b) at least one fatty acid salt (soap) and
  c) at least one oxyethylenated fatty alcohol of formula (I) below:

$$CH_3(CH_2)_x-CH_2-(CH_2CH_2OH)_y-OH \quad (I)$$

in which x is an integer greater than 20 and preferably ranging from 21 to 30 and y varies from 1 to 20 and
  d) at least one fragrancing substance.
The present invention also relates to a method of stabilizing a fragrancing aqueous transparent solid composition comprising, in a cosmetically acceptable support:
  a) at least one aqueous phase and
  b) at least one fatty acid salt and
  c) at least one fragrancing substance, characterized by the fact that it comprises adding, to said composition, at least one polyoxyethylenated fatty alcohol of formula (I).

19 Claims, 1 Drawing Sheet

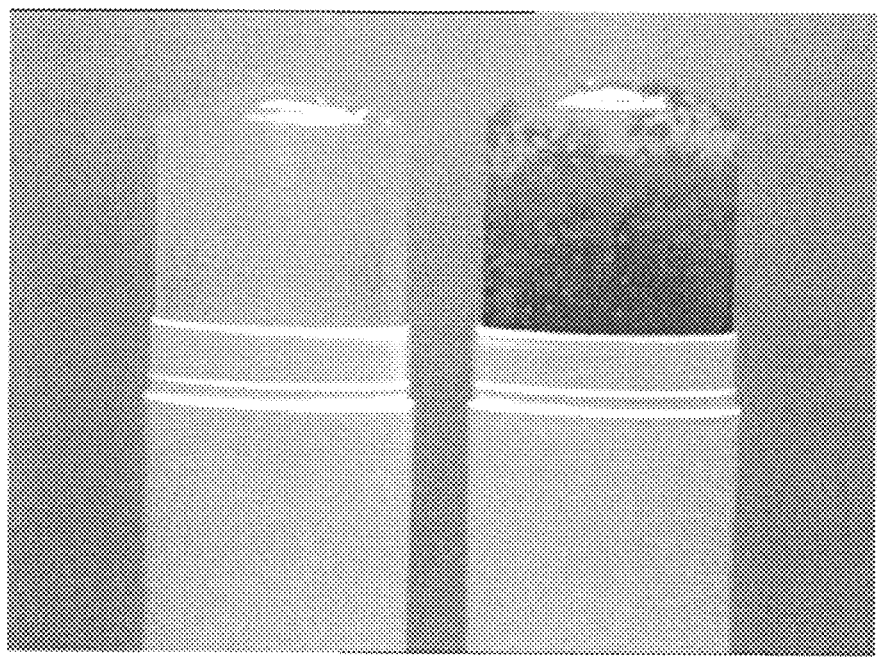

FRAGRANCING TRANSPARENT SOLID COMPOSITION BASED ON FATTY ACID SALTS AND ON AN OXYETHYLENATED FATTY ALCOHOL; AND STABILIZATION METHOD

The invention relates to a fragrancing aqueous transparent solid composition in a cosmetically acceptable support:
- a) at least one aqueous phase and
- b) at least one fatty acid salt (soap) and
- c) at least one oxyethylenated fatty alcohol of particular formula (I) and
- d) at least one fragrancing substance.

In the cosmetic field, it is well known to use, in topical application, transparent or translucent solid products (sticks) especially in the field of body hygiene such as deodorant sticks.

Aqueous translucent or transparent sticks based on fatty acid salts or soaps are particularly sought after for their cosmetic qualities and their transparent appearance which, for the consumer, is simultaneously suggestive of the clarity, the cleanliness and the efficacy of the product. They have especially been described in U.S. Pat. Nos. 4,559,924; 5,114,717; 5,120,541, 4,440,742; 5,128,123; 4,504,465; 4,226,889, 4,702,916; 4,732,754. It is important that the appearance of the stick (i.e. homogeneity, transparency) is able to remain stable over time under the storage and usage conditions.

Deodorant sticks having a transparency that is stable over time are known from U.S. Pat. No. 5,863,524 which are based on fatty acid salts, bicarbonate salt and alkali metal salt and a clarifying agent of polyamine type. Aqueous sticks having a transparency that is stable over time based on fatty acid salts, a polyoxyalkylenated fatty alcohol of the Eumulgin type such as Ceteareth-30 or PPG-2-ceteareth-9 are also known. It has also been proposed, in U.S. Pat. No. 5,407,668, to use a mixture constituted of an alkanolamide and a monoalkoxylated fatty alcohol in order to reinforce the transparency and the stability of the transparency in soap-based deodorant sticks.

For the comfort and pleasure of the user, transparent aqueous sticks based on fatty acid salts generally comprise, in addition, fragrances. In the course of its research, the Applicant has observed that the presence of fragrance could lead to a great increase in the acid number and in the formation over time of crystals within the matrix of the stick and render the latter heterogeneous, cloudy and opaque.

Therefore, there remains a need to search for novel aqueous fragranced solid compositions based on fatty acid salts that do not exhibit the drawbacks of the products of the prior art, namely for which the homogeneity and/or the transparency remains stable over time.

The Applicant has surprisingly discovered that it was possible to achieve this objective using an oxyethylenated fatty alcohol of formula (I), which will be defined below in detail, in a solid composition based on fatty acid salts and comprising at least one fragrancing substance.

This discovery constitutes the basis for the invention.

The present invention therefore relates to a fragrancing aqueous transparent solid composition comprising, in a cosmetically acceptable support:
- a) at least one aqueous phase and
- b) at least one fatty acid salt and
- c) at least one oxyethylenated fatty alcohol of formula (I) that will be defined below in detail and
- d) at least one fragrancing substance.

The present invention also relates to a method of stabilizing a fragrancing aqueous transparent solid composition comprising, in a cosmetically acceptable support:
- a) at least one aqueous phase and
- b) at least one fatty acid salt and
- c) at least one fragrancing substance, characterized by the fact that it comprises adding, to said composition, at least one polyoxyethylenated fatty alcohol of formula (I) that will be defined below in detail.

SUMMARY OF DRAWING

FIG. 1 shows a solid deodorant composition (Ex 1) that is not within the scope of the invention and a solid deodorant composition (Ex 2) that is within the scope of the present invention.

Other subjects of the invention will appear in the remainder of the description.

The expression "fragrancing composition" is understood to mean any composition that leaves a fragrance after application to keratin materials.

The expression "fragrancing substance" is understood to mean any fragrance or aroma capable of fragrancing the skin and human keratin materials in general including the skin, the hair, the scalp, the lips and the nails.

The expression "cosmetically acceptable support" is understood to mean a non-toxic medium capable of being applied to human keratin materials including the skin, the face, the lips, the nails, the hair and the scalp.

The term "transparent" is understood to mean a composition having a turbidity of less than 400 NTU (Nephelometric Turbidity Units) at 25° C. and preferably of less than 250 NTU at 25° C., measured with a 2100P Turbidimeter machine from HACH.

The expression "solid composition" is understood to mean that the measurement of the maximum force measured in texture analysis during the insertion of a probe down into the formulation sample should be at least equal to 0.25 newton, in particular at least equal to 0.30 newton, especially at least equal to 0.35 newton, assessed under precise measurement conditions as follows:

The formulations are hot-cast into pots 4 cm in diameter and 3 cm deep. Cooling takes place at ambient temperature. The hardness of the formulations prepared is measured after waiting for 24 hours. The pots containing the samples are characterized by texture analysis using a texture analyser such as that sold by the company Rhéo TA-XT2, according to the following protocol: a stainless steel bead type probe having a diameter of 5 mm is brought into contact with the sample at a speed of 1 mm/s. The measurement system detects the interface with the sample with a detection threshold equal to 0.005 newton. The probe is pushed down 0.3 mm into the sample at a speed of 0.1 mm/s. The measuring device records the change in the force, measured in compression, over time, during the penetration phase. The hardness of the sample corresponds to the average of the maximum values of the force detected during the penetration, over at least 3 measurements.

Soaps

The fatty acid salt or soap is obtained from a fatty acid and a base, the fatty acid comprising a saturated or unsaturated, linear or branched alkyl chain having from 12 to 22 carbon atoms and preferably 12 to 20 carbon atoms.

The bases (also known as saponifiers) completely or partially neutralize the fatty acids. The bases capable of being used to obtain the salts may be, for example, inorganic bases such as alkali metal hydroxides (sodium hydroxide and potassium hydroxide), alkaline-earth metal hydroxides (magnesium hydroxide) or ammonium hydroxide, or else organic bases such as triethanolamine, N-methylglucamine, lysine and arginine. According to one particular embodiment of the invention, the base is potassium hydroxide.

The soap is generally introduced into the composition in the form of the base on the one hand and of the fatty acid on the other hand, the formation of the salt taking place in situ.

The degree of neutralization of the fatty acid is defined as being the weight ratio between the fatty acids in the form of salts and the total fatty acids (free acids plus fatty acid salts). In the composition according to the invention, this degree of neutralization preferably ranges from 80 to 97%, and better still from 85 to 95%.

The fatty acid may be chosen, in particular, from $C_{10}$ to $C_{24}$ and especially $C_{12}$-$C_{18}$ fatty acids and in particular lauric acid, myristic acid, stearic acid, palmitic acid and mixtures thereof.

As soaps, mention may be made, for example, of the potassium salts and the sodium salts of $C_{10}$-$C_{24}$, especially $C_{12}$-$C_{20}$, more especially $C_{12}$-$C_{18}$ fatty acids. The soap may be more especially the sodium salts of $C_{12}$-$C_{18}$ fatty acids, more especially the sodium salt of stearic acid.

The total amount of fatty acid salts in the composition of the invention varies preferably from 0.5 to 20% by weight and better still from 1 to 10% by weight relative to the total weight of the composition.

Oxyethylenated Fatty Alcohol

The oxyethylenated fatty alcohols according to the invention correspond to the general formula (I) below:

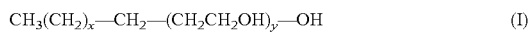

$$CH_3(CH_2)_x-CH_2-(CH_2CH_2OH)_y-OH \quad (I)$$

in which x is an integer greater than 19 and preferably ranging from 20 to 30 and y varies from 1 to 20.

According to one particularly preferred form, use will be made of an oxyethylenated behenyl alcohol corresponding to the general formula (I') below:

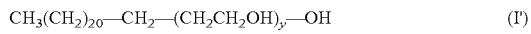

$$CH_3(CH_2)_{20}-CH_2-(CH_2CH_2OH)_y-OH \quad (I')$$

in which y varies from 1 to 20 and more preferably from 1 to 10.

Among the oxyethylenated behenyl alcohols, mention may be made of the following compounds:
Beheneth-1, Beheneth-2, Beheneth-3, Beheneth-4, Beheneth-5, Beheneth-6, Beheneth-7, Beheneth-8, Beheneth-9, Beheneth-10, Beheneth-11, Beheneth-12, Beheneth-13, Beheneth-14, Beheneth-15, Beheneth-16, Beheneth-17, Beheneth-18, Beheneth-19, Beheneth-20.

As commercial products, mention may be made of:
- the products sold under the names EMULGIN BA (+the ethoxylation number) by the company Cognis such as for example EUMULGIN BA 10 for Beheneth-10 and EUMULGIN BA 20 for Beheneth-20;
- the products sold under the names NIKKOL BB (+the ethoxylation number) by the company Nikko Chemicals such as for example NIKKOL BB 20 for Beheneth-20; and
- the products sold under the names EMALEX BHA by the company Nihon Emulsion such as for example EUMULGIN-BA 10 for Beheneth-10.

Use will more particularly be made of Beheneth-10.

The amount of oxyethylenated fatty alcohol of formula (I) varies preferably from 0.1 to 10% by weight and more preferably from 0.5 to 2% by weight relative to the total weight of the composition.

Fragrances

As the fragrancing substance, it is possible to use, in the composition of the invention, fragrances and aromas of natural or synthetic origin and mixes thereof. As fragrances and aromas of natural origin, mention may be made, for example, of extracts of flowers (lily, lavender, rose, jasmine, ylang-ylang), of stems and of leaves (patchouli, geranium, petit-grain), of fruits (coriander, anise, cumin, juniper), of fruit peels (bergamot, lemon, orange), of roots (angelica, celery, cardamom, iris, calamus), of wood (pine wood, sandalwood, guaiac, pink cedar), of herbs and grasses (tarragon, lemon-grass, sage, thyme), of needles and branches (spruce, fir, pine, dwarf pine), of resins and balsams (galbanum, elemi gum, benzoin, myrrh, frankincense, opopanax).

As a fragrancing substance of synthetic origin, mention may be made, for example, of compounds of ester, ether, aldehyde, ketone, aromatic alcohol and hydrocarbon type.

As esters, mention may be made, in particular, of benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styralyl propionate and benzyl salicylate.

As ethers, mention may be made of benzyl ethyl ether.

As aldehydes, mention may be made, for example, of linear alkanals comprising from 8 to 18 carbon atoms, citral, citronellal, citronellyl oxyacetaldehyde, cyclamen aldehyde, hydroxycitronellal, lilial and bourgeonal.

As ketones, mention may be made, for example, of ionones such as alpha-isomethylionone, and methyl cedryl ketone.

Among the aromatic and notably terpene alcohols, mention may be made of anethol, citronellol, eugenol, isoeugenol, geraniol, linalool, phenylethyl alcohol and terpineol.

As hydrocarbons, mention may especially be made of terpenes. These compounds are often in the form of a mixture of two or more of these odorous substances.

Furthermore, use may also be made of essential oils, components of aromas such as, for example, the essential oils of sage, of camomile, of clove, of lemon balm, of mint, of cinnamon leaves, of lime blossom, of juniper, of vetiver, of frankincense, of galbanum, of labolanum and of lavandin.

As a fragrancing substance it is possible to use, alone or as a mixture, bergamot essential oil, dihydromyrecenol, lilial, lyral, citronellol, phenylethyl alcohol, alpha-hexylcinnamaldehyde, geraniol, benzyl acetone, cyclamen aldehyde, linalool, ambroxan, indole, hedione, sandelice, lemon, mandarin and orange essential oils, allylamine glycolate, cyclovertal, lavandin essential oil, sage essential oil, beta-damascone, geranium essential oil, cyclohexyl salicylate, phenylacetic acid, geranyl acetate, benzyl acetate or rose oxide.

It is also possible to use a mixture of various fragrancing substances which together produce an agreeable note for the user. Among the known olfactory notes, mention may be made, for example, of hesperidic fragrances, aromatics, floral fragrances, musks, fruity fragrances, spices, oriental fragrances, marine fragrances, aquatic notes, chypre fragrances, woody fragrances, fougères and mixtures thereof.

The amount of fragrancing substance(s) will be more preferably from 0.5 to 30% by weight, better still from 0.5 to 10%, even better still from 0.5 to 5% by weight relative to the total weight of the composition.

Deodorant Active Agents

According to one particular form of the invention, the compositions according to the invention comprise, in addition, at least one deodorant active agent.

Within the meaning of the present invention, the expression "deodorant active agent" is understood to mean any substance capable of masking, absorbing, improving or reducing the unpleasant odour resulting from the decomposition of human sweat by bacteria.

The deodorant active agents may be bacteriostatic agents or bactericidal agents, such as 2,4,4'-trichloro-2'-hydroxy-diphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropane-tetraacetic acid) or 1,2 decanediol (SIMCLARIOL from Symrise).

Among the deodorant active agents in accordance with the invention, mention may also be made of:
- zinc salts such as zinc salicylate, zinc gluconate, zinc pidolate, zinc sulphate, zinc chloride, zinc lactate or zinc phenolsulphonate;
- chlorhexidine and salts thereof;
- sodium bicarbonate;
- salicylic acid and derivatives thereof such as 5-n-octanoylsalicylic acid;
- glycerol derivatives such as, for example, caprylic/capric glycerides (CAPMUL MCM from Abitec), glycerol caprylate or caprate (DERMOSOFT GMCY and DERMOSOFT GMC respectively from Straetmans), polyglyceryl-2 caprate (DERMOSOFT DGMC from Straetmans); and
- biguanide derivatives, such as polyhexamethylene biguanide salts.

In the event of incompatibility or in order to stabilize them, some of the active agents mentioned above may be incorporated into spheroids, especially ionic or non-ionic vesicles and/or nanoparticles (nanocapsules and/or nanospheres).

The deodorant active agents may preferably be present in the compositions according to the invention in weight concentrations ranging from 0.01 to 5% by weight relative to the total weight of the composition.

Aqueous Phase

Within the meaning of the invention, the expression "aqueous phase" is understood to mean the water and all of the ingredients of the composition of the invention that are soluble in water.

The water will preferably vary in concentrations ranging from 10 to 40% by weight relative to the total weight of the composition.

According to one preferred form of the invention, the aqueous phase may contain at least one $C_1$-$C_4$ monoalcohol and/or at least one polyol.

Among the $C_1$-$C_4$ monoalcohols, mention will be made, for example, of methanol, ethanol, propanol and isopropanol. Use will preferably be made of ethanol. The monoalcohols will preferably be present at concentrations ranging from 3 to 50% by weight.

Among the polyols, mention may be made, for example, of ethylene glycol, glycerol, erythritol, propylene glycol, 1,3-propanediol, mannitol, sorbitol, xylitol, maltitol and lactitol.

The polyols will preferably be present at concentrations from 40 to 70% by weight relative to the total weight of the composition.

Additives

The composition according to the invention may also contain other ingredients that are well known in the field of deodorant cosmetic products, of which mention may be made, for example, of soothing agents, preservatives, antioxidants, sequestrants, hydrophilic thickeners or gelling agents, hydrophilic active agents and mixtures thereof.

As the customary active agents in the cosmetic or dermatological field which may be used according to the invention, mention may be made, in particular, of all the active agents known for their activity with respect to skin ageing such as keratolytic or prodesquamating agents, for example α-hydroxy acids such as lactic acid, citric acid and glycolic acid, β-hydroxy acids such as salicylic acid and derivatives thereof, α-keto acids, β-keto acids; retinoids and esters thereof, such as retinol and esters thereof, retinal or karotenoids. Mention may also be made of the 15 vitamins, such as, for example, the vitamins A, $B_3$, PP, B5, E, K1 and/or C and the derivatives of these vitamins and in particular the esters thereof; free-radical scavengers, moisturizing agents such as natural extracts; procyanidolic oligomers; protein hydrolysates; sugar derivatives; and hydrophilic sunscreens.

As gelling agents, use may in particular be made of hydrophilic gelling agents such as carboxyvinyl polymers, for instance carbomers; polyacrylamides and 2-acrylamido-2-methylpropanesulphonic acid polymers and copolymers, which are optionally crosslinked and/or neutralized, such as poly(2-acrylamido-2-methylpropane-sulphonic acid) sold by Clariant under the trade name "Hostacerin AMPS" (CTFA name: ammonium polyacryldimethyltauramide); or the acrylamide/sodium acrylamido-2-methylpropanesulphonate copolymer as a 40% inverse emulsion in polysorbate, sold under the name SIMULGEL 600 by SEPPIC; polysaccharides such as xanthan gum; and mixtures thereof.

The invention is illustrated in greater detail in the following examples. The amounts are given as weight percentages relative to the total weight of the composition.

EXAMPLES

The following deodorant transparent solid compositions were produced

| INGREDIENTS | Ex. 1: not part of the invention without oxyethylenated fatty alcohol | Ex. 2: invention with Beheneth-10 | Ex. 3: invention with Beheneth-20 | Ex. 4: not part of the invention with Beheneth-30 | Ex. 5: not part of the invention with Steareth-10 | Ex. 6: not part of the invention without fragrance |
|---|---|---|---|---|---|---|
| Deodorant active agent | 1 | 1 | 1 | 1 | 1 | 1 |
| EDTA | 0.5 | 0.5 | 0.5 | 0.5 | 0.5 | 0.5 |
| GLYCEROL | 20 | 20 | 20 | 20 | 20 | 20 |
| PROPYLENE GLYCOL | 50 | 50 | 50 | 50 | 50 | 50 |
| SODIUM STEARATE | 5 | 5 | 5 | 5 | 5 | 5 |
| STEARETH-100 | 1 | 1 | 1 | 1 | 1 | 1 |
| BEHENIC ACID | 2 | 2 | 2 | 2 | 2 | 2 |
| FRAGRANCE (FREZENTE SBM 34829 GESXE - FIRMENICH) | 1 | 1 | 1 | 1 | 1 | |

-continued

| INGREDIENTS | Ex. 1: not part of the invention without oxyethylenated fatty alcohol | Ex. 2: invention with Beheneth-10 | Ex. 3: invention with Beheneth-20 | Ex. 4: not part of the invention with Beheneth-30 | Ex. 5: not part of the invention with Steareth-10 | Ex. 6: not part of the invention without fragrance |
|---|---|---|---|---|---|---|
| BEHENETH-10 (EUMELGIN BA-10) | | 1 | | | | |
| BEHENETH-20 (NIKKOL BB-20) | | | 1 | | | |
| BEHENETH-30 (EMALEX BHA-30) | | | | 1 | | |
| STEARETH-10 (BRIJ 76 - CRODA) | | | | | 1 | |
| SODIUM HYDROXIDE | qs for pH | qs for pH | qs for pH | qs for pH | qs for pH | qs for pH |
| WATER | qs for 100 | qs for 100 | qs for 100 | qs for 100 | qs for 100 | qs for 100 |

Transparent deodorant sticks were produced according to the following procedure:

Procedure

The glycerol and the propylene glycol are introduced into a beaker, with stirring.

The mixture is heated at 85° C.

The sodium stearate, behenic acid, deodorant active agent, EDTA, Steareth-100 and alkoxylated fatty alcohol are added, with stirring.

The temperature is lowered to 65° C. and the fragrance is added.

The acid number is adjusted between 0 and 0.2 mg KOH/g using sodium hydroxide pellets and the mixture is topped up with water.

The sticks are cast at 65° C. in the packaging article.

Transparency Stability Tests

A test is carried out on formulations 1 to 6 for measuring the change in the acid number over time and at temperature.

The tests carried out are essentially measurements of the change of the acid number over time and at temperatures in order to catalyze the hydrolysis of the esters.

A/Method for Measuring the Acid Number:

The initial formulation is placed on a hot plate and brought to 66° C., the initial acid number is then adjusted between 0 and 0.1 mg of KOH/g.

A sample of the solution is taken at the end of 6 hours at 66° C. in order to evaluate the increase of the acid number during these 6 hours.

The assay of the acid number is measured according to the method below:

1—Principle

The acid number measures the amount of free acid functional groups that can be titrated by a solution of sodium hydroxide.

2—Reagents
Titrant: 0.1N NaOH
Solvent: 96° ethanol is used as solvent for the sample to be assayed 3—Equipment
METTLER DL 53 type memo-titrator or equivalent
Electrode: Mettler-Toledo DG111-SC
Titration vessel
Burette having a volume of 10 ml suited to the assumed value of the acid number 4—Procedure
Around 20 g exactly of the solid composition to be assayed is weighed. 60 ml of ethanol is added and the sample is dissolved with stirring and at high temperature. The mixture is assayed using the 0.1N NaOH solution by following the change in potential.

The acid number is calculated according to the following equation:

$$\text{Acid number mg KOH/g} = \frac{56.1 \times V \times T}{P}$$

with
P (g): test sample
V (ml): volume poured for the test
T: actual titre of the titrant used The increase in the acid number is determined by the following calculation Increase in the acid number = acid number after 6 h − acid number at $t=0$ B/Method for Measuring the Transparency:

After storing at 25° C. for 6 months, the transparency of formulations 1 to 6 is measured with a 2100P Turbidimeter machine from HACH. It is expressed in Nephelometric Turbidity Units (NTU).

Results

The results are indicated in the following table:

| | Ex. 1: not part of the invention | Ex. 2: invention | Ex. 3: invention | Ex. 4: not part of the invention | Ex. 5: not part of the invention | Ex. 6: not part of the invention without fragrance |
|---|---|---|---|---|---|---|
| Increase in the acid number after 6 hours (mg KOH/g) | 0.136 | 0.071 | 0.121 | 0.149 | 0.137 | 0 |
| Transparency after 6 months (NTU) | >1000 | <100 | <400 | >1000 | >1000 | <100 |

The appearance of sticks 1 and 2 after 6 months was photographed and is shown in FIG. 1.

The invention claimed is:

1. A fragrancing aqueous transparent solid composition comprising, in a cosmetically acceptable support:
   a) at least one aqueous phase,
   b) at least one fatty acid salt,
   c) at least one oxyethylenated behenyl alcohol of formula (I') below:

$$CH_3(CH_2)_{20}-CH_2-(CH_2CH_2OH)_y-OH \quad (I')$$

in which y varies from 1 to 20 and
   d) at least one fragrancing substance.

2. The composition according to claim 1, wherein the fatty acid salt is chosen from potassium salts and sodium salts of $C_{10}$-$C_{24}$.

3. The composition according to claim 2, wherein the fatty acid salt is chosen from the sodium salts of $C_{12}$-$C_{18}$ fatty acids.

4. The composition according to any one of claim 1, wherein the total amount of fatty acid salts varies from 0.5 to 20% by weight of the composition.

5. The composition according to claim 1 wherein in the formula (I') below:

$$CH_3(CH_2)_{20}-CH_2-(CH_2CH_2OH)_y-OH \quad (I'),$$

y varies from 1 to 10.

6. The composition according to claim 5, wherein the oxyethylenated fatty alcohol is Beheneth-10.

7. The composition according to claim 1, wherein the amount of oxyethylenated fatty alcohol of formula (I) varies from 0.1 to 10% by weight relative to the total weight of the composition.

8. The composition according to claim 1, wherein the amount of fragrancing substance(s) varies from 0.5 to 30% by weight relative to the total weight of the composition.

9. The composition according to claim 1, comprising, in addition, a deodorant active agent.

10. The composition according to claim 1, to 9, in which the water varies in concentrations ranging from 10 to 40% by weight relative to the total weight of the composition.

11. The composition according to claim 1, in which the aqueous phase comprises, in addition, at least one $C_1$-$C_4$ monoalcohol and/or at least one polyol.

12. The composition according to claim 11, in which the monoalcohol or monoalcohols are present in concentrations ranging from 3 to 50% by weight relative to the total weight of the composition.

13. The composition according to claim 11, in which the polyol or polyols are present in concentrations ranging from 40 to 70% by weight relative to the total weight of the composition.

14. A method of stabilizing a fragrancing aqueous transparent solid composition comprising, in a cosmetically acceptable support:
   a) at least one aqueous phase,
   b) at least one fatty acid salt as defined in claim 1, and
   c) at least one fragrancing substance, wherein the method comprises adding, to said composition, d) at least one polyoxyethylenated behenyl alcohol of formula (I') as defined in claim 1.

15. The composition according to claim 1, wherein the fatty acid salt is chosen from potassium salts and sodium salts of $C_{12}$-$C_{20}$.

16. The composition according to claim 1, wherein the fatty acid salt is chosen from potassium salts and sodium salts of $C_{12}$-$C_{18}$ fatty acids.

17. The composition according to claim 2, wherein the fatty acid salt is chosen from the sodium salt of stearic acid.

18. The composition according to claim 1, wherein the total amount of fatty acid salts varies from 1 to 10% by weight to the total weight of the composition.

19. The composition according to claim 1, wherein the amount of oxyethylenated behenyl alcohol of formula (I') varies from 0.5 to 2% by weight relative to the total weight of the composition.

* * * * *